United States Patent
Chopiuk et al.

(10) Patent No.: US 7,189,729 B2
(45) Date of Patent: Mar. 13, 2007

(54) METHODS AND COMPOSITIONS AS PROTEIN KINASE INHIBITORS

(75) Inventors: Greg Chopiuk, San Diego, CA (US); Pascal Furet, Thann (FR); Nathanael Schiander Gray, San Diego, CA (US); Patricia Imbach, Kaiseraugst (CH); Yi Liu, San Diego, CA (US); Joseph Schoepfer, Riehen (CH); Ruo Steensma, La Jolla, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 10/956,412

(22) Filed: Sep. 30, 2004

(65) Prior Publication Data

US 2005/0171105 A1    Aug. 4, 2005

Related U.S. Application Data

(60) Provisional application No. 60/507,592, filed on Sep. 30, 2003.

(51) Int. Cl.
  *C07D 239/42* (2006.01)
  *C07D 403/12* (2006.01)
  *A61K 31/506* (2006.01)
  *A61P 19/02* (2006.01)
  *A61P 35/00* (2006.01)

(52) U.S. Cl. ...................... 514/256; 544/326; 544/328; 544/333

(58) Field of Classification Search ................ 544/326, 544/328, 333; 514/256
  See application file for complete search history.

(56) References Cited

U.S. PATENT DOCUMENTS

2002/0052386 A1    2/2002    Armistead et al.
2004/0116388 A1    6/2004    Armistead et al.

FOREIGN PATENT DOCUMENTS

WO    WO-01/60816 A1 *    8/2001

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*
Mass, R. D., Int. J. Radiation Oncology Bio. Phys.vol. 58(3): 932-940, 2004.*
Fabbro et al. Pharmacology & therapeutics 93, 79-98, 2002.*

* cited by examiner

*Primary Examiner*—Venkataraman Balasubramanian
(74) *Attorney, Agent, or Firm*—Scott W. Reid; The Genomics Institute of the Novartis Research Foundation

(57) ABSTRACT

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Abl, BCR-Abl, EGF-R, c-erbB2 kinase (HER-2), CHK2, FGFR3, p70S6K, PKC, PDGF-R, p38, TGFβ, KDR, c-Kit, b-RAF, c-RAF, FLT1 and/or FLT4 kinases.

7 Claims, No Drawings

METHODS AND COMPOSITIONS AS PROTEIN KINASE INHIBITORS

CROSS-REFERENCE TO RELATED APPLICATIONS

This application claims the benefit of priority under 35 U.S.C. §119(e) to U.S. Provisional Patent Application No. 60/507,592, filed Sep. 30, 2003. The disclosure of the priority application is incorporated herein by reference in its entirety and for all purposes.

FIELD OF THE INVENTION

This application claims the benefit of priority under 35 U.S.C. §119(e) to U.S. Provisional Patent Application No. 60/486,134, filed Jul. 10, 2003. The disclosure of the priority application is incorporated herein by reference in its entirety and for all purposes. The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Abl, BCR-Abl, EGF-R, c-erbB2 kinase (HER-2), CHK2, FGFR3, p70S6K, PKC, PDGF-R, p38, TGFβ, KDR, c-Kit, b-RAF, c-RAF, FLT1 and/or FLT4 kinases.

BACKGROUND

The protein kinases represent a large family of proteins, which play a central role in the regulation of a wide variety of cellular processes and maintaining control over cellular function. A partial, non-limiting, list of these kinases include: receptor tyrosine kinases such as platelet-derived growth factor receptor kinase (PDGF-R), c-erbB2 kinase (HER-2), VEGF-receptor kinase (e.g. KDR, Flt-1 and Flt-4), TGFβ, Epidermal Growth factor Receptor (EGF-R), the receptor kinase for stem cell factor, c-kit; non-receptor tyrosine kinases such Abl and the fusion kinase BCR-Abl; and serine/threonine kinases such asp38, b-RAF and c-RAF. Aberrant kinase activity has been observed in many disease states including benign and malignant proliferative disorders as well as diseases resulting from inappropriate activation of the immune and nervous systems.

The novel compounds of this invention inhibit the activity of one or more protein kinases and are, therefore, expected to be useful in the treatment of kinase-associated diseases.

SUMMARY OF THE INVENTION

In one aspect, the present invention provides compounds of formula I:

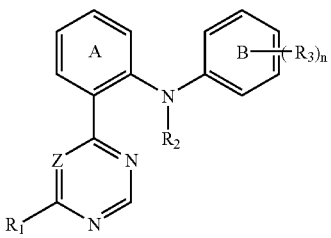

in which:
n is 0, 1, 2 or 3;
Z is selected from =N— and =CH—;
$R_1$ is selected from hydrogen and —$NR_4R_5$; wherein $R_4$ is selected from hydrogen and $C_{1-6}$alkyl; and $R_5$ is selected from $C_{6-10}$aryl, $C_{5-10}$heteroaryl, $C_{3-12}$cycloalkyl and $C_{3-8}$heterocycloalkyl, wherein any aryl, heteroaryl, cycloalkyl or heterocycloalkyl of $R_5$ can be optionally substituted by 1 to 3 radicals independently selected from cyano, nitro, halo, $C_{1-6}$alkyl, halo-substituted-$C_{1-6}$alkyl, $C_{1-6}$alkoxy, halo-substituted-$C_{1-6}$alkoxy and —$NR_6R_7$; wherein $R_6$ and $R_7$ are independently selected from hydrogen and $C_{1-6}$alkyl;
$R_2$ is selected from hydrogen and $C_{1-6}$alkyl;
$R_3$ is selected from halo, cyano, nitro, $C_{1-6}$alkyl, halo-substituted-$C_{1-6}$alkyl, $C_{1-6}$alkoxy, halo-substituted-$C_{1-6}$alkoxy, —$XNR_8R_8$, —$XNR_8R_9$, —$XC(O)R_8$, —$XNR_8C(O)R_9$ and —$XC(O)NR_8R_9$; wherein X is a bond or $C_{1-4}$alkylene, $R_8$ is selected from hydrogen and $C_{1-6}$alkyl, and $R_9$ is selected from $C_{6-10}$aryl, $C_{5-10}$heteroaryl, $C_{3-12}$cycloalkyl and $C_{3-8}$heterocycloalkyl; wherein any aryl, heteroaryl, cycloalkyl or heterocycloalkyl of $R_9$ is optionally substituted by a radical selected from halo-substituted-$C_{1-6}$ alkyl, —$XOR_8$, —$XR_{10}$, —$XS(O)_2N(OR_8)_2$, —$XS(O)N(XOR_8)_2$, —$XSN(OR_8)_2$, —$XSR_{10}$, —$XS(O)R_{10}$ and —$XS(O)_2R_{10}$; wherein X is a bond or $C_{1-6}$alkylene, $R_8$ is hydrogen or $C_{1-6}$alkyl, and $R_{10}$ is a radical selected from $C_{3-8}$heterocycloalkyl and $C_{5-10}$heteroaryl; wherein any heterocycloalkyl or heteroaryl of $R_{10}$ is optionally substituted by 1 to 3 radicals independently selected from halo, cyano, nitro, $C_{1-6}$alkyl, halo-substituted-$C_{1-6}$alkyl, $C_{1-6}$alkoxy, halo-substituted-$C_{1-6}$alkoxy; and any one ring carbon of $R_{10}$ is optionally replaced by —C(O)—; and wherein the phenyl rings A and B can have up to four —C= groups replaced by —N=; and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which inhibition of kinase activity, particularly Abl, BCR-Abl, EGF-R, c-erbB2 kinase (HER-2), CHK2, FGFR3, p70S6K, PKC, PDGF-R, p38, TGFβ, KDR, c-Kit, b-RAF, c-RAF, FLT1 and/or FLT4 activity, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which kinase activity, particularly Abl, BCR-Abl, EGF-R, c-erbB2 kinase (HER-2), CHK2, FGFR3, p70S6K, PKC, PDGF-R, p38, TGFβ, KDR, c-Kit, b-RAF, c-RAF, FLT1 and/or FLT4 activity, contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group. "Heteroaryl" is as defined for aryl where one or more of the ring members are a heteroatom. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, etc.

"Halogen" (or halo) preferably represents chloro or fluoro, but may also be bromo or iodo.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of kinase related disease, particularly Abl, BCR-Abl, EGF-R, c-erbB2 kinase (HER-2), CHK2, FGFR3, p70S6K, PKC, PDGF-R, p38, TGFβ, KDR, c-Kit, b-RAF, c-RAF, FLT1 and/or FLT4 kinase related diseases. For example, leukemia and other proliferation disorders related to BCR-Abl can be treated through the inhibition of wild type and mutant forms of Bcr-Abl.

In one embodiment, with reference to compounds of Formula I, $R_1$ is selected from hydrogen and —NR$_4$R$_5$; wherein $R_4$ is selected from hydrogen and $C_{1-6}$alkyl; and $R_5$ is $C_{6-10}$aryl optionally substituted by 1 to 3 radicals independently selected from halo-substituted -$C_{1-6}$alkyl and —NR$_6$R$_7$; wherein $R_6$ and $R_7$ are independently selected from hydrogen and $C_{1-6}$alkyl; and $R_2$ is selected from hydrogen and $C_{1-6}$alkyl;

$R_3$ is selected from halo, $C_{1-6}$alkyl, —XC(O)R$_8$, —XNR$_8$R$_8$, —XNR$_8$C(O)R$_9$ and —XC(O)NR$_8$R$_9$; wherein X is a bond or $C_{1-4}$alkylene, $R_8$ is selected from hydrogen and $C_{1-6}$alkyl, and $R_9$ is selected from $C_{6-10}$aryl and $C_{3-12}$cycloalkyl; wherein any aryl or cycloalkyl of $R_9$ is optionally substituted by a radical selected from —XOR$_8$, —XR$_{10}$, —XS(O)$_2$N(XOR$_8$)$_2$ and —XS(O)$_2$R$_{10}$; wherein X is a bond or $C_{1-6}$alkylene, $R_8$ is hydrogen or $C_{1-6}$alkyl, and $R_{10}$ is a radical selected from $C_{3-8}$heterocycloalkyl and $C_{5-10}$heteroaryl; wherein any heterocycloalkyl or heteroaryl of $R_{10}$ is optionally substituted by 1 to 3 $C_{1-6}$alkyl groups; and any one ring carbon of $R_{10}$ is optionally replaced by —C(O)—.

In another embodiment, $R_1$ is selected from hydrogen and —NHR$_5$; wherein $R_5$ is phenyl optionally substituted by 1 to 3 radicals independently selected from trifluoromethyl and dimethylamino; and $R_2$ is hydrogen.

In a further embodiment, $R_3$ is selected from halo, methyl, formyl, dimethylamino, —NHC(O)R$_9$ and —C(O)NHR$_9$; wherein $R_9$ is selected from phenyl and cyclopropyl; wherein any aryl or cycloalkyl of $R_9$ is optionally substituted by a radical selected from —CH$_2$OH, —XR$_{10}$, —S(O)$_2$N(C$_2$H$_4$OH)$_2$ and —S(O)$_2$R$_{10}$; wherein X is a bond or methylene, and $R_{10}$ is a radical selected from piperazinyl, morpholino and 5-oxo-4,5-dihydro-pyrazol-1-yl; wherein any heterocycloalkyl or heteroaryl of $R_{10}$ is optionally substituted by 1 to 3 methyl groups.

In another embodiment, $R_4$ is selected from halo, trifluoromethyl and —XR$_{10}$; wherein X is a bond or methylene; $R_{10}$ is selected from imidazolyl, piperazinyl and morpholino; wherein any heteroaryl or heterocycloalkyl is optionally substituted with methyl.

Preferred compounds of Formula I are selected from: N-(3-{2-[6-(3-Dimethylamino-phenylamino)-pyrimidin-4-yl]-phenylamino}-phenyl)-4-(4-methyl-piperazin-1-ylmethyl)-benzamide; N-(3-{2-[6-(4-Trifluoromethyl-phenylamino)-pyrimidin-4-yl]-phenylamino}-phenyl)-benzamide; 4-(4-Methyl-piperazin-1-ylmethyl)-N-(3-{2-[6-(4-trifluoromethyl-phenylamino)-pyrimidin-4-yl]-phenylamino}-phenyl)-benzamide; N-(3-{2-[6-(3-Dimethylamino-phenylamino)-pyrimidin-4-yl]-phenylamino}-phenyl)-4-hydroxymethyl-benzamide; N-(3-{2-[6-(3-Dimethylamino-phenylamino)-pyrimidin-4-yl]-phenylamino}-phenyl)-3-(morpholine-4-sulfonyl)-benzamide; N-(3-{2-[6-(3-Dimethylamino-phenylamino)-pyrimidin-4-yl]-phenylamino}-phenyl)-4-(3-methyl-5-oxo-4,5-dihydro-pyrazol-1-yl)-benzamide; N-(3-{2-[6-(3-Dimethylamino-phenylamino)-pyrimidin-4-yl]-phenylamino}-phenyl)-3-(4-methyl-piperazine-1-sulfonyl)-benzamide; 4-[B is-(2-hydroxy-ethyl)-sulfamoyl]-N-(3-{2-[6-(3-dimethylamino-phenylamino)-pyrimidin-4-yl]-phenylamino}-phenyl)-benzamide; 4-(4-Methyl-piperazin-1-ylmethyl)-N-[3-(2-pyrimidin-4-yl-phenylamino)-phenyl]-benzamide; N-Cyclopropyl-3-{2-[6-(4-trifluoromethyl-phenylamino)-pyrimidin-4-yl]-phenylamino}-benzamide; {6-[2-(3-Fluoro-phenylamino)-phenyl]-pyrimidin-4-yl}-(4-trifluoromethyl-phenyl)-amine; {6-[2-(2-Fluoro-phenylamino)-phenyl]-pyrimidin-4-yl}-(4-trifluoromethyl-phenyl)-amine; {6-[2-(4-Fluoro-phenylamino)-phenyl]-pyrimidin-4-yl}-(4-trifluoromethyl-phenyl)-amine; {6-[2-(2-Chloro-phenylamino)-phenyl]-pyrimidin-4-yl}-(4-trifluoromethyl-phenyl)-amine; {6-[2-(3-Chloro-phenylamino)-phenyl]-pyrimidin-4-yl}-(4-trifluoromethyl-phenyl)-amine; {6-[2-(4-Chloro-phenylamino)-phenyl]-pyrimidin-4-yl}-(4-trifluoromethyl-phenyl)-amine; [6-(2-o-Tolylamino-phenyl)-pyrimidin-4-yl]-(4-trifluoromethyl-phenyl)-amine; [6-(2-m-Tolylamino-phenyl)-pyrimidin-4-yl]-(4-trifluoromethyl-phenyl)-amine; [6-(2-p-Tolylamino-phenyl)-pyrimidin-4-yl]-(4-trifluoromethyl-phenyl)-amine; 3-{2-[6-(4-Trifluoromethyl-phenylamino)-pyrimidin-4-yl]- phenylamino}-benzaldehyde; 4-{2-[6-(4-Trifluoromethyl-phenylamino)-pyrimidin-4-yl]-phenylamino}-benzaldehyde; (4-Trifluoromethyl-phenyl)-{6-[2-(2-trifluoromethyl-phenylamino)-phenyl]-pyrimidin-4-yl}-amine; (4-Trifluoromethyl-phenyl)-{6-[2-(4-trifluoromethyl-phenylamino)-phenyl]-pyrimidin-4-yl}-amine; N,N-Dimethyl-N'-{2-[6-(4-trifluoromethyl-phenylamino)-pyrimidin-4-yl]-phenyl}-benzene-1,4-diamine; Phenyl-[6-(2-phenylamino-phenyl)-pyrimidin-4-yl]-amine; {6-[2-(2,6-Dichloro-phenylamino)-phenyl]-pyrimidin-4-yl}-(3,4,5-trimethoxy-phenyl)-amine; and {6-[2-(2,6-Dichloro-phenylamino)-phenyl]-pyrimidin-4-yl}-[4-(4-methyl-piperazin-1-yl)-phenyl]-amine.

Further preferred compounds of Formula I are detailed in the Example and Table I, infra.

Pharmacology and Utility

Compounds of the invention modulate the activity of protein tyrosine kinases and, as such, are useful for treating diseases or disorders in which protein tyrosine kinases, particularly Abl, BCR-Abl, EGF-R, c-erbB2 kinase (HER-2), CHK2, FGFR3, p70S6K, PKC, PDGF-R, p38, TGFβ, KDR, c-Kit, b-RAF, c-RAF, FLT1 and/or FLT4 kinases, contribute to the pathology and/or symptomology of the disease.

Abelson tyrosine kinase (i.e. Abl, c-Abl) is involved in the regulation of the cell cycle, in the cellular response to genotoxic stress, and in the transmission of information about the cellular environment through integrin signaling. Overall, it appears that the Abl protein serves a complex role as a cellular module that integrates signals from various extracellular and intracellular sources and that influences decisions in regard to cell cycle and apoptosis. Abelson tyrosine kinase includes sub-types derivatives such as the chimeric fusion (oncoprotein) BCR-Abl with deregulated tyrosine kinase activity or the v-Abl. BCR-Abl is critical in the pathogenesis of 95% of chronic myelogenous leukemia (CML) and 10% of acute lymphocytic leukemia. STI-571 (Gleevec) is an inhibitor of the oncogenic BCR-Abl tyrosine kinase and is used for the treatment of chronic myeloid leukemia (CML). However, some patients in the blast crisis stage of CML are resistant to STI-571 due to mutations in the BCR-Abl kinase. Over 22 mutations have been reported to date with the most common being G250E, E255V, T315I, F317L and M351T.

Compounds of the present invention inhibit abl kinase, especially v-abl kinase. The compounds of the present invention also inhibit wild-type BCR-Abl kinase and mutations of BCR-Abl kinase and are thus suitable for the treatment of Bcr-abl-positive cancer and tumor diseases, such as leukemias (especially chronic myeloid leukemia and acute lymphoblastic leukemia, where especially apoptotic mechanisms of action are found), and also shows effects on the subgroup of leukemic stem cells as well as potential for the purification of these cells in vitro after removal of said cells (for example, bone marrow removal) and reimplantation of the cells once they have been cleared of cancer cells (for example, reimplantation of purified bone marrow cells).

PDGF (Platelet-derived Growth Factor) is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis. Compounds of the invention can inhibit PDGF receptor (PDGFR) activity and are, therefore, suitable for the treatment of tumor diseases, such as gliomas, sarcomas, prostate tumors, and tumors of the colon, breast, and ovary.

Compounds of the present invention, can be used not only as a tumor-inhibiting substance, for example in small cell lung cancer, but also as an agent to treat non-malignant proliferative disorders, such as atherosclerosis, thrombosis, psoriasis, scleroderma and fibrosis, as well as for the protection of stem cells, for example to combat the hemotoxic effect of chemotherapeutic agents, such as 5-fluoruracil, and in asthma. Compounds of the invention can especially be used for the treatment of diseases, which respond to an inhibition of the PDGF receptor kinase.

Compounds of the present invention show useful effects in the treatment of disorders arising as a result of transplantation, for example, allogenic transplantation, especially tissue rejection, such as especially obliterative bronchiolitis (OB), i.e. a chronic rejection of allogenic lung transplants. In contrast to patients without OB, those with OB often show an elevated PDGF concentration in bronchoalveolar lavage fluids.

Compounds of the present invention are also effective in diseases associated with vascular smooth-muscle cell migration and proliferation (where PDGF and PDGF-R often also play a role), such as restenosis and atherosclerosis. These effects and the consequences thereof for the proliferation or migration of vascular smooth-muscle cells in vitro and in vivo can be demonstrated by administration of the compounds of the present invention, and also by investigating its effect on the thickening of the vascular intima following mechanical injury in vivo.

The compounds of the present invention also inhibit cellular processes involving stem-cell factor (SCF, also known as the c-kit ligand or steel factor), such as inhibiting SCF receptor (kit) autophosphorylation and SCF-stimulated activation of MAPK kinase (mitogen-activated protein kinase). MO7e cells are a human promegakaryocytic leukemia cell line, which depends on SCF for proliferation. Compounds of the invention can inhibit the autophosphorylation of SCF receptors.

The Ras-Raf-MEK-ERK signaling pathway mediates cellular response to growth signals. Ras is mutated to an oncogenic form in ~15% of human cancer. The Raf family belongs to the serine/threonine protein kinase and it includes three members, A-Raf, B-Raf and c-Raf (or Raf-1). The focus on Raf being a drug target has centered on the relationship of Raf as a downstream effector of Ras. However, recent data suggests that B-Raf may have a prominent role in the formation of certain tumors with no requirement for an activated Ras allele (Nature 417, 949–954 (01 Jul. 2002). In particular, B-Raf mutations have been detected in a large percentage of malignant melanomas.

Existing medical treatments for melanoma are limited in their effectiveness, especially for late stage melanomas. The compounds of the present invention also inhibit cellular processes involving b-Raf kinase, providing a new therapeutic opportunity for treatment of human cancers, especially for melanoma.

The compounds of the present invention also inhibit cellular processes involving c-Raf kinase. c-Raf is activated by the ras oncogene, which is mutated in a wide number of human cancers. Therefore inhibition of the kinase activity of c-Raf may provide a way to prevent ras mediated tumor growth [Campbell, S. L., Oncogene, 17, 1395 (1998)].

The compounds of the present invention also inhibit cellular processes involving KDR, Flt-1 and Flt-4. A number of diseases are known which are associated with deregulated angiogenesis, for example diseases caused by ocular neovascularisation, especially retinopathies (diabetic retinopathy, age-related macular degeneration); psoriasis; haemangioblastomas, such as "strawberry-marks" (=haemangioma); various inflammatory diseases, such as arthritis, especially rheumatoid arthritis, arterial atherosclerosis and atherosclerosis occurring after transplants, endometriosis or chronic asthma; and, especially, tumor diseases (solid tumors, but also leukemias and other liquid tumors, since many primitive blood cells and leukemia cells express c-kit, KDR, Flt-1 and Flt-4). Flt-4 is expressed in developing lymphatic vessels. Only the lymphatic endothelia and some high endothelial venules express Flt4 mRNA in adult human tissues and increased expression occurs in lymphatic sinuses in metastatic lymph nodes and in lymphangioma. Inhibition of KDR-mediated functional effects by inhibiting KDR's catalytic activity is considered to be an important therapeutic strategy in the treatment of angiogenized disease states including cancer.

Multiple forms of p38 MAPK (α, β, γ, δ), each encoded by a separate gene, form part of a kinase cascade involved in the response of cells to a variety of stimuli, including osmotic stress, UV light and cytokine mediated events. These four isoforms of p38 are thought to regulate different aspects of intracellular signaling. Its activation is part of a cascade of signaling events that lead to the synthesis and production of pro-inflammatory cytokines like TNFα. P38 functions by phosphorylating downstream substrates that include other kinases and transcription factors. Agents that inhibit p38 kinase have been shown to block the production of cytokines including but not limited to TNFα, IL-6, IL-8 and IL-1β. Peripheral blood monocytes (PBMCs) have been shown to express and secrete pro-inflammatory cytokines when stimulated with lipopolysaccharide (LPS) in vitro. P38 inhibitors efficiently block this effect when PBMCs are pretreated with such compounds prior to stimulation with LPS. P38 inhibitors are efficacious in animal models of inflammatory disease. The destructive effects of many disease states are caused by the over production of pro-inflammatory cytokines. The ability of p38 inhibitors to regulate this overproduction makes them useful as disease modifying agents.

Molecules that block p38's function have been shown to be effective in inhibiting bone resorption, inflammation, and other immune and inflammation-based pathologies. Thus, a safe and effective p38 inhibitor would provide a means to treat debilitating diseases that can be regulated by modulation of p38 signaling like, for example, RA. Therefore, compounds of the invention that inhibit p38 activity are useful for the treatment of inflammation, osteoarthritis, rheumatoid arthritis, cancer, autoimmune diseases, and for the treatment of other cytokine mediated diseases.

Transforming growth factor-beta (TGFβ) denotes a superfamily of proteins that includes, for example, TGFβ1, TGFβ2, and TGFβ3, which are pleotropic modulators of cell growth and differentiation, embryonic and bone development, extracellular matrix formation, hematopoiesis, immune and inflammatory responses. The members of the TGFβ family initiate intracellular signaling pathways leading ultimately to the expression of genes that regulate the cell cycle, control proliferative responses, or relate to extracellular matrix proteins that mediate outside-in cell signaling, cell adhesion, migration and intercellular communication. Consequently, compounds of the invention that are inhibitors of the TGFβ intracellular signaling pathway are useful treatments for fibroproliferative diseases, including kidney disorders associated with unregulated TGFβ activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, scleroderma, dermatomyositis, eosinophilic fascitis, morphea, or those associated with the occurrence of Raynaud's syndrome. Lung fibroses resulting from excessive TGFβ activity include adult respiratory distress syndrome, COPD, idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis. Fibroproliferative conditions can be associated with surgical eye procedures. Such procedures include retinal reattachment surgery accompanying proliferative vitreoretinopathy, cataract extraction with intraocular lens implantation, and post glaucoma drainage surgery.

Fibroblast growth factor receptor 3 was shown to exert a negative regulatory effect on bone growth and an inhibition of chondrocyte proliferation. Thanatophoric dysplasia is caused by different mutations in fibroblast growth factor receptor 3, and one mutation, TDII FGFR3, has a constitutive tyrosine kinase activity which activates the transcription factor Stat1, leading to expression of a cell-cycle inhibitor, growth arrest and abnormal bone development (Su et al., Nature, 1997, 386, 288–292). FGFR3 is also often expressed in multiple myeloma-type cancers.

The kinase, c-Src transmits oncogenic signals of many receptors. For example, over-expression of EGFR or HER2/neu in tumors leads to the constitutive activation of c-src, which is characteristic for the malignant cell but absent from the normal cell. On the other hand, mice deficient in the expression of c-src exhibit an osteopetrotic phenotype, indicating a key participation of c-src in osteoclast function and a possible involvement in related disorders.

The cell cycle checkpoint kinase Chk2 is activated by DNA damage and activated Chk2 phosphorylates and thereby inactivates Cdc25C. Cells without active Chk2 have a defect in their checkpoint response to DNA damage. The inactivation of Chk2 abrogates the G2/M arrest which is induced by damaged DNA and sensitizes the resulting checkpoint deficient cells to the killing by DNA damaging events. As cancer cells are more sensitive towards the abrogation of the G2/M checkpoint than normal cells there is great interest in compounds which inhibit Chk2 and improve the killing of cancer cells by DNA damaging events.

The family of human ribosomal S6 protein kinases consists of at least 8 members (RSK1, RSK2, RSK3, RSK4, MSK1, MSK2, p70S6K and p70S6 Kb). Ribosomal protein S6 protein kinases play important pleotropic functions, among them is a key role in the regulation of mRNA translation during protein biosynthesis (Eur. J. Biochem 2000 November;267(21): 6321–30, Exp Cell Res. Nov.25, 1999; 253 (1):100–9, Mol Cell Endocrinol. May 25, 1999; 151(1–2):65–77). The phosphorylation of the S6 ribosomal protein by p70S6 has also been implicated in the regulation of cell motility (Immunol. Cell Biol. 2000 August;78(4): 447–51) and cell growth (Prog. Nucleic Acid Res. Mol. Biol., 2000;65:101–27), and hence, may be important in tumor metastasis, the immune response and tissue repair as well as other disease conditions.

In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other agents that prevent or treat any of the diseases or disorders described above. These include immunomodulatory or anti-inflammatory substances, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA4Ig. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I, in which $R_5$ is hydrogen, can be prepared by proceeding as in the following Reaction Scheme I:

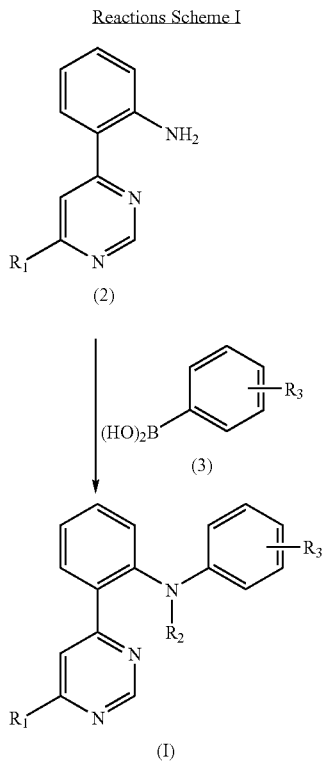

in which $R_1$, $R_2$ and $R_3$ are as defined for Formula I in the Summary of the Invention.

A compound of the invention (Formula I) can be prepared by reacting a compound of formula 2 with a compound of formula 3 in the presence of a suitable solvent (e.g., methylene chloride, and the like), an appropriate amine (e.g., diisopropylethylamine, and the like), using an appropriate catalyst (copper (II) acetate, and the like). The reaction is carried out in the temperature range of 10 to 50° C. and can take up to about 24 hours to complete. A detailed description of the synthesis of a compound of Formula I is set forth in the examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction schemes I; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;

(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I according to the invention.

Example 1

N-(3-{2-[6-(3-Dimethylamino-phenylamino)-pyrimidin-4-yl]-phenylamino}-phenyl)-4-(4-methyl-piperazin-1-ylmethyl)-benzamide

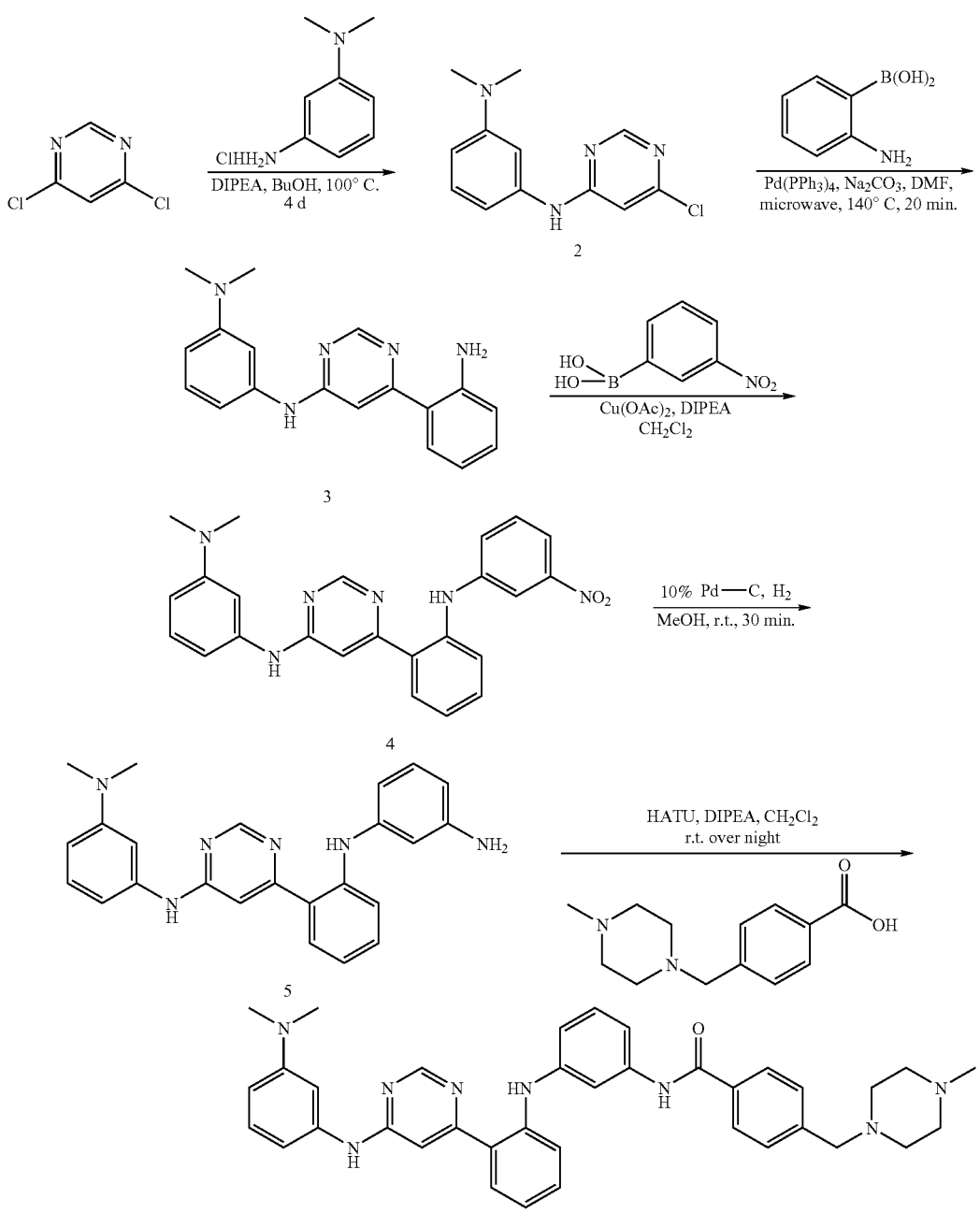

Example 1

A mixture of 3-(N,N-dimethylamine)aniline (10.0 g, 0.040 mol) and diisopropylethylamine (15.7 g, 0.121 mol) in butanol (400 mL) is heated to 100° C. 4,6-Dichloropyrimidine (7.81 g, 0.0524 mol) is added slowly over a 20-minute period. White gas and solvent boiling is observed during the addition. The resulting solution is stirred for 24 hours and the pH measurement indicates acidic conditions. More diisopropylethylamine (7.81 g, 0.0524 mol) is added and the reaction mixture is stirred for another 24 hours. The pH measurement again indicates an acidic mixture, more diisopropylethylamine (7.81 g, 0.0524 mol) is added and the mixture stirred for another 24 hours. The reaction mixture is rapidly cooled and the solvent is removed under vacuum. The remaining yellow residue is dissolved in ethyl acetate (100 mL) and washed with water (3×). The organic phase is dried over magnesium sulfate, filtered and concentrated until a large amount of precipitate appears. The solid is isolated by filtration, washed with hexanes and dried on a high vacuum for 24 hours to give compound 2 (7.02 g, 70%); MS m/z (M+H$^+$) 249.10.

To a mixture of compound 2 (100 mg, 0.4 mmol), 2-(boronic acid) aniline (110 mg, 0.8 mmol) in N,N-dimethylformide (5 mL) is added tetrakis-(triphenylphosphine)-palladium (0) (93 mg, 0.08 mmol) and 4M sodium carbonate (1.6 mL, 1.6 mmol). The tube is sealed and placed in the microwave for 1200 seconds at 140° C. The mixture is then poured into brine (10 mL) and extracted with ethyl acetate (3×). The organic layers are combined, washed with brine and dried over magnesium sulfate. After filtration, the organic solvent is removed and the crude product is purified by silica gel chromatography to give compound 3 (100 mg, 81%); MS m/z (M+H$^+$) 306.1.

A mixture of compound 3 (150 mg, 0.5 mmol), 3-nitrobenzene boronic acid (250 mg, 1.5 mmol), copper (II) acetate (45 mg, 0.25 mmol) and diisopropylethylamine (250 mg, 2.0 mmol) in methylene chloride (10 mL) is stirred at room temperature over night. The mixture is diluted with methylene chloride and washed with saturated sodium bicarbonate. The organic portion is dried over magnesium sulfate, filtered and concentrated. The crude product is then purified by silica gel chromatography (neat methylene chloride) to afford compound 4 (150 mg, 71% yield); MS m/z (M+H$^+$) 427.10.

A mixture of compound 4 (150 mg, 0.35 mmol) and 10% Pd-C (15 mg) in methanol (10 mL) was stirred under hydrogen (1 atmosphere) at room temperature for 30 minutes. Palladium catalyst was removed by filtration and the methanol solution was concentrated to dryness to afford compound 5 (100 mg, 77% yield) as yellow syrup; MS m/z (M+H$^+$) 397.30.

A mixture of compound 5 (20 mg, 0.05 mmol), 4-(N-methyl-piperazyl)-methyl-benzoic acid (14 mg, 0.06 mmol), O-(7-azabenzotriazol-1-yl)-N,N,N',N'-tetramethyl-uronium hexafluorophosphate (23 mg, 0.06 mmol) and diisopropyl-ethylamine (8 mg, 0.06 mmol) in methylene chloride (2 mL) is stirred at room temperature over night. LCMS purification afforded N-(3-{2-[6-(3-dimethylamino-phenylamino)-pyrimidin-4-yl]-phenylamino}-phenyl)-4-(4-methyl-piperazin-1-ylmethyl)-benzamide (9.2 mg, 30 % yield):

$^1$H NMR 400 Hz (CDCl$_3$) δ 2.51 (s, 3H), 2.61 (br, 4H), 2.78 (br, 4H), 2.97 (s, 6H), 3.58 (s, 2H), 6.57 (m, 1H), 6.68 (m, 2H), 6.84 (m, 1H), 6.97 (m, 1H), 7.10 (m, 2H), 7.18 (m, 1H), 7.26 (m, 2H), 7.40 (d, J=8.12 Hz, 2H), 7.46 (d, J=8.12 Hz, 2H), 7.54 (s, br, 1H), 7.79 (d, J=8.14 Hz, 2H), 7.86 (s, 1H), 8.69 (s, 1H); MS m/z (M+H$^+$) 613.30.

By repeating the procedures described in the above examples, using appropriate starting materials, the following compounds of Formula I, as identified in Table 1, are obtained.

TABLE 1

| Compound Number | Structure | Physical Data $^1$H NMR 400 MHz (DMSO-d$_6$) and/or MS (m/z) |
|---|---|---|
| 1 | 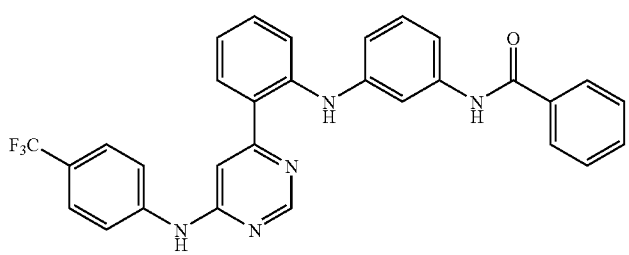 | $^1$H NMR 400 Hz (CD$_3$OD) δ 6.78 (d, J=7.94 Hz, 1H), 7.08 (m, 2H), 7.19 (m, 2H), 7.45 (m, 4H), 7.58 (m, 5H), 7.85 (m, 4H), 8.74 (s, 1H). MS m/z (M + H$^+$) 526.20 |
| 2 | 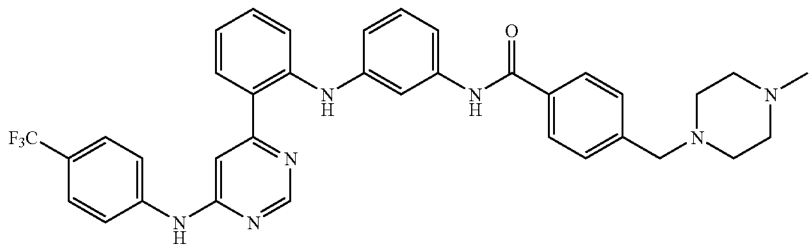 | $^1$H NMR 400 Hz (CDCl$_3$) δ 2.35 (s, 3H), 2.52 (br, 8H), 3.57 (s, 2H), 6.88 (t, J=7.12 Hz, 1H), 6.98 (dd, J=1.34, 8.00 Hz, 1H), 7.07 (s, 1H), 7.11 (dd, J=1.10, 7.95 Hz, 1H), 7.26 (m, 3H), 7.48 (m, 5H), 7.62 (m, 5H), 7.79 (m, 3H), 8.78 (d, J=0.74 Hz, 1H). MS m/z (M + H$^+$) 638.20 |

TABLE 1-continued

| Compound Number | Structure | Physical Data<br>¹H NMR 400 MHz (DMSO-d₆) and/or MS (m/z) |
|---|---|---|
| 4 | 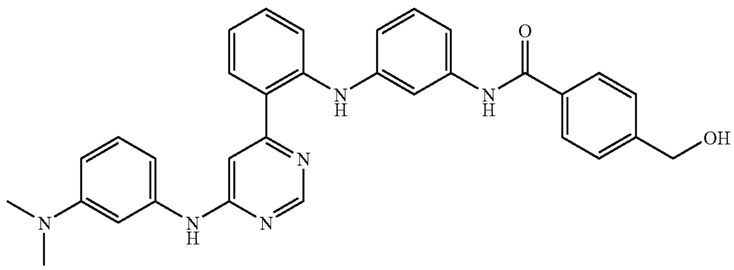 | ¹H NMR 400 Hz (CD₃OD) δ 2.90 (s, 6H), 4.67 (s, 2H), 6.53 (m, 1H), 6.85 (m, 2H), 6.95 (m, 2H), 7.04 (d, J=1.06 Hz, 1H), 7.13 (t, J=8.13 Hz, 1H), 7.19 (m, 2H), 7.30 (m, 1H), 7.47 (m, 5H), 7.88 (d, J=8.29 Hz, 2H), 8.58 (d, J=1.07 Hz, 1H). MS m/z (M + H⁺) 531.30 |
| 5 | 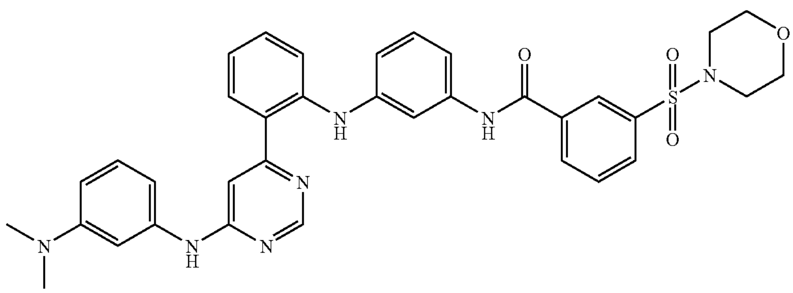 | ¹H NMR 400 Hz (CD₃OD) δ 2.96 (s, 6H), 2.99 (dd, J=4.38, 5.05 Hz, 4H), 3.69 (dd, J=4.53, 4.81 Hz, 4H), 6.75 (m, 2H), 6.90 (br, 1H), 7.05 (m, 3H), 7.18 (m, 3H), 7.42 (m, 1H), 7.52 (m, 3H), 7.75 (t, J=7.82 Hz, 1H), 7.95 (d, J=8.29 Hz, 1H), 8.16 (d, J=7.9 Hz, 1H), 8.25 (s, 1H), 8.64 (s, 1H). MS m/z (M + H⁺) 650.25 |
| 6 | 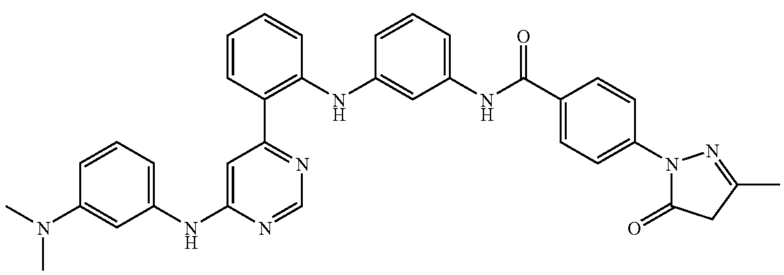 | MS m/z (M + H⁺) 597.20 |
| 7 | 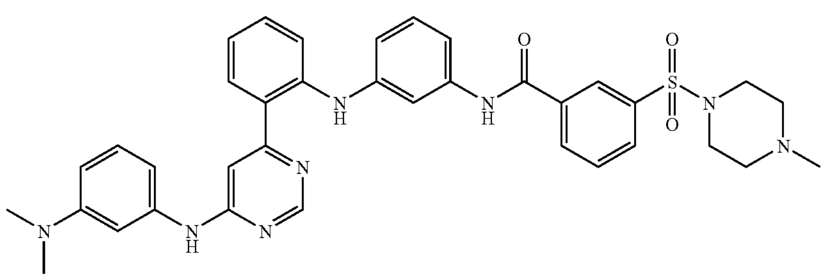 | ¹H NMR 400 Hz (CD₃OD) δ 2.88 (s, 3H), 2.98 (s, 6H), 3.03 (br, 4H), 3.45 (br, 4H), 6.76 (m, 2H), 6.95 (br, 1H), 7.09 (m, 3H), 7.20 (m, 3H), 7.44 (m, 1H), 7.52 (m, 3H), 7.77 (t, J=7.85 Hz, 1H), 7.99 (m, 1H), 8.20 (m, 1H), 8.30 (s, 1H), 8.65 (s, 1H). MS m/z (M + H⁺) 663.20 |
| 8 | 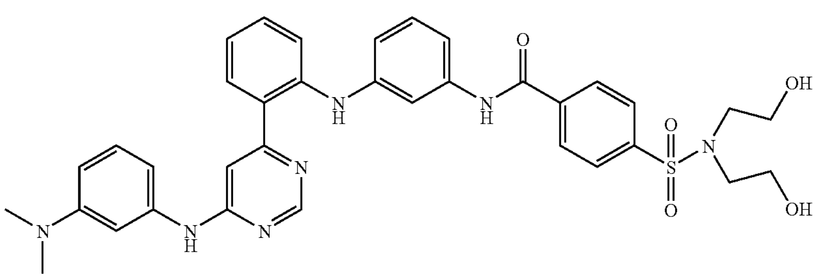 | ¹H NMR 400 Hz (CD₃OD) δ 2.91 (s, 6H), 3.34 (m, 4H), 3.72 (t, J=5.86 Hz, 4H), 6.84 (m, 1H), 6.86 (m, 2H), 6.98 (m, 2H), 7.06 (s, 1H), 7.18 (m, 3H), 7.34 (m, 1H), 7.42 (d, J=8.25 Hz, 1H), 7.54 (m, 2H), 7.95 (m, 2H), 8.05 (d, J=8.41 Hz, 2H), 8.59 (s, 1H). MS m/z (M + H⁺) 667.30 |

TABLE 1-continued

| Compound Number | Structure | Physical Data $^1$H NMR 400 MHz (DMSO-$d_6$) and/or MS (m/z) |
|---|---|---|
| 9 | 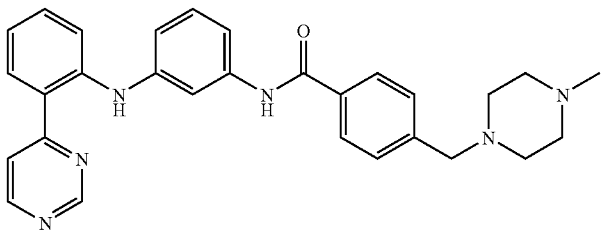 | $^1$H NMR 400 Hz (CD$_3$OD) δ 2.91 (s, 3H), 2.98 (br, 4H), 3.38 (br, 4H), 3.57 (s, 2H), 6.97 (m, 2H), 7.26 (m, 2H), 7.39 (t, J=1.37 Hz, 1H), 7.47 (d, J=7.71 Hz, 1H), 7.55 (d, J=8.27 Hz, 2H), 7.65 (s, 1H), 7.86 (d, J=9.34 Hz, 1H), 7.94 (d, J=8.26 Hz, 2H), 8.02 (d, J=5.50 Hz, 1H), 8.77 (br, 1H), 9.24 (br, 1H). MS m/z (M + H$^+$) 479.20. |
| 10 | 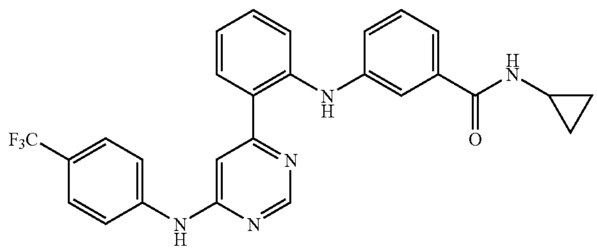 | MS m/z (M + H$^+$) 490.20 |
| 11 | 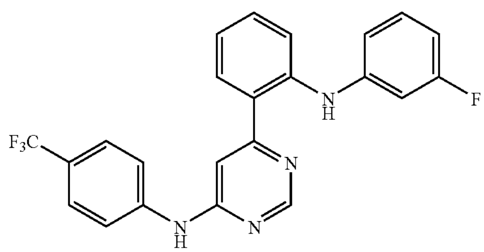 | MS m/z (M + H$^+$) 425.10 |
| 12 | 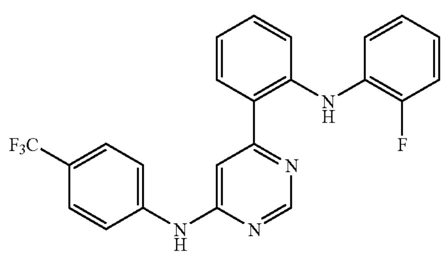 | MS m/z (M + H$^+$) 425.10 |
| 13 | 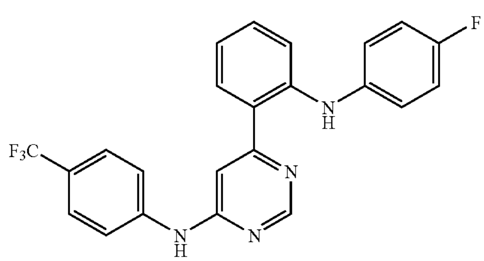 | $^1$H NMR 400 Hz (CD$_3$OD) δ 6.84 (m, 5H), 7.09 (s, 1H), 7.16 (d, J=7.39 Hz, 1H), 7.29 (t, J=8.50 Hz, 1H), 7.45 (m, 1H), 7.55 (d, J=8.58 Hz, 2H), 7.80 (d, J=8.52 Hz, 2H), 8.71 (s, 1H). MS m/z (M + H$^+$) 425.10425.10 |
| 14 | 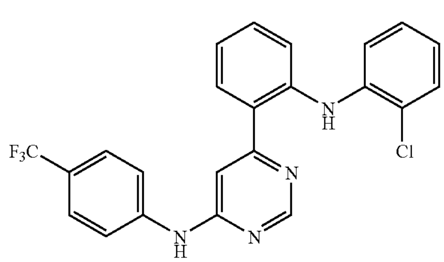 | MS m/z (M + H$^+$) 441.10 |

TABLE 1-continued

| Compound Number | Structure | Physical Data ¹H NMR 400 MHz (DMSO-$d_6$) and/or MS (m/z) |
|---|---|---|
| 15 | 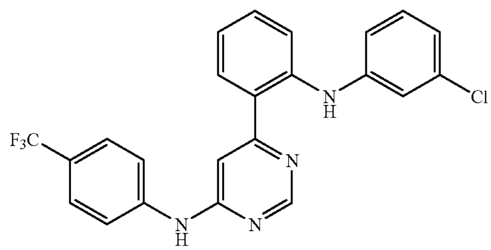 | MS m/z (M + H$^+$) 441.10 |
| 16 | 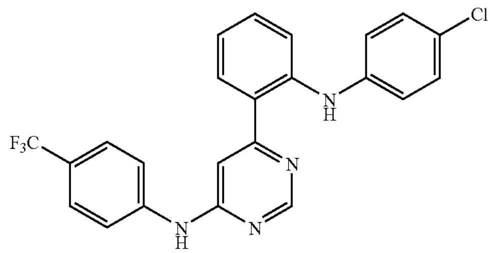 | MS m/z (M + H$^+$) 441.10 |
| 17 | 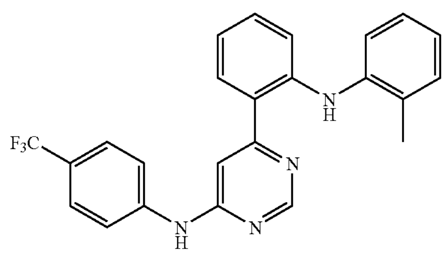 | MS m/z (M + H$^+$) 421.10 |
| 18 | 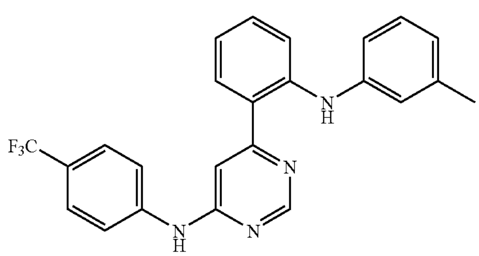 | MS m/z (M + H$^+$) 421.20 |
| 19 | 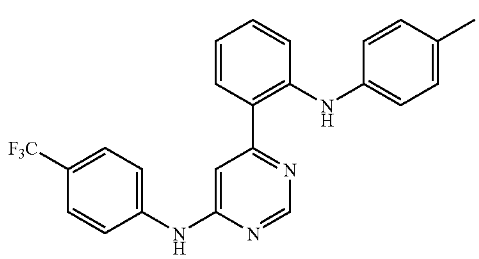 | ¹H NMR 400 Hz (CD$_3$OD) δ 2.42 (s, 3H), 7.11 (d, J=8.23 Hz, 2H), 7.20 (m, 3H), 7.35 (br, 1H), 7.47 (d, J=8.14 Hz, 1H), 7.57 (t, J=7.40 Hz, 1H), 7.67 (d, J=7.55 Hz, 1H), 7.81 (d, J=8.56 Hz, 2H), 8.02 (d, J=8.50 Hz, 2H), 8.97 (br, 1H). MS m/z (M + H$^+$) 421.20 |

TABLE 1-continued

| Compound Number | Structure | Physical Data <br> ¹H NMR 400 MHz (DMSO-d₆) and/or MS (m/z) |
| --- | --- | --- |
| 20 | 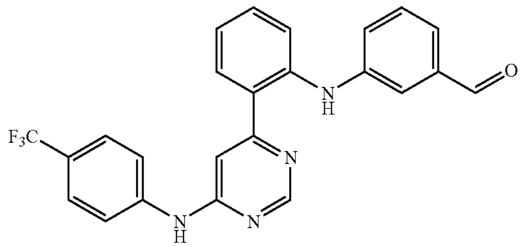 | MS m/z (M + H⁺) 435.10 |
| 21 | 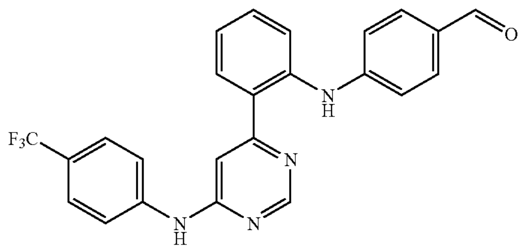 | MS m/z (M + H⁺) 435.10 |
| 22 | 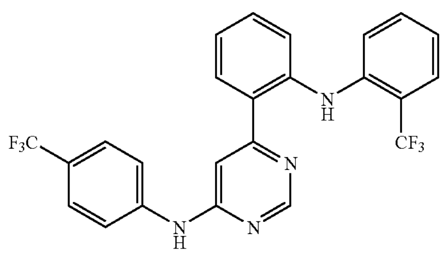 | ¹H NMR 400 Hz (CD₃OD) δ 6.91 (t, J=7.59 Hz, 1H), 7.00 (m, 2H), 7.19 (d, J=8.24 Hz, 1H), 7.29 (m, 3H), 7.53 (m, 4H), 7.77 (d, J=8.52 Hz, 2H), 8.62 (s, 1H). MS m/z (M + H⁺) 475.10 |
| 23 | 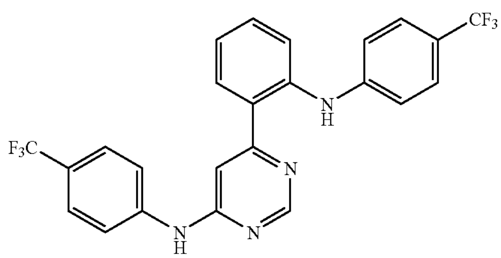 | MS m/z (M + H⁺) 475.10 |
| 24 | 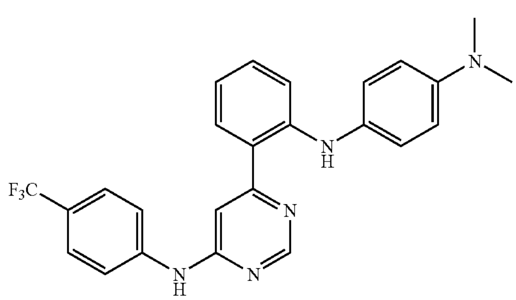 | ¹H NMR 400 Hz (CD₃OD) δ 3.01 (s, 6H), 7.08 (m, 2H), 7.20 (s, 1H), 7.41 (m, 4H), 7.48 (m, 1H), 7.55 (d, J=8.58 Hz, 2H), 7.67 (m, 1H), 7.75 (d, J=8.49 Hz, 2H), 8.72 (s, 1H). MS m/z (M + H⁺) 450.20 |

TABLE 1-continued

| Compound Number | Structure | Physical Data $^1$H NMR 400 MHz (DMSO-$d_6$) and/or MS (m/z) |
|---|---|---|
| 25 | 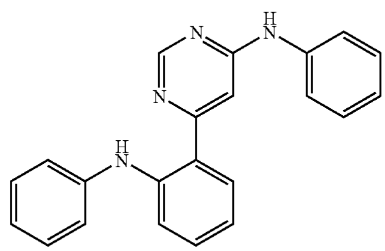 | $^1$H-NMR (400 MHz, ClCl$_3$) 6.79, t, 1H, 6.88, s, 1H, 6.96, t, 1H; 7.13–7.75, m, 12H; 8.71 s, 1H, 10.20, s, 1H; MS m/z (M + H$^+$) 339.2. |
| 26 | 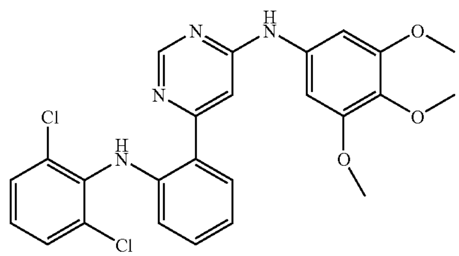 | MS m/z (M + H$^+$) 504.9 |
| 27 | 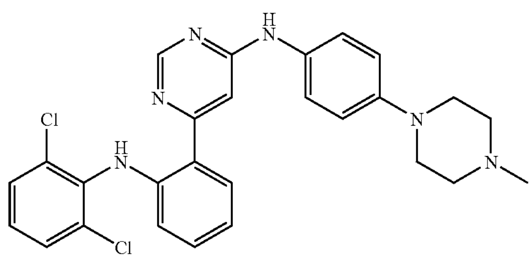 | MS m/z (M + H$^+$) 496.9 |

Assays

Compounds of the present invention are assayed to measure their capacity to selectively inhibit cell proliferation of 32D cells expressing BCR-Abl (32D-p210) compared with parental 32D cells. Compounds selectively inhibiting the proliferation of these BCR-Abl transformed cells are tested for anti-proliferative activity on Ba/F3 cells expressing either wild type or the mutant forms of Bcr-abl. In addition, compounds are assayed to measure their capacity to inhibit b-Raf.

Inhibition of Cellular BCR-Abl Dependent Proliferation (High Throughput Method)

The murine cell line used is the 32D hemopoietic progenitor cell line transformed with BCR-Abl cDNA (32D-p210). These cells are maintained in RPMI/10% fetal calf serum (RPMI/FCS) supplemented with penicillin 50 μg/mL, streptomycin 50 μg/mL and L-glutamine 200 mM. Untransformed 32D cells are similarly maintained with the addition of 15% of WEHI conditioned medium as a source of IL3.

50 μl of a 32D or 32D-p210 cells suspension are plated in Greiner 384 well microplates (black) at a density of 5000 cells per well. 50 nl of test compound (1 mM in DMSO stock solution) is added to each well (STI571 is included as a positive control). The cells are incubated for 72 hours at 37° C., 5% CO$_2$. 10 μl of a 60% Alamar Blue solution (Tek diagnostics) is added to each well and the cells are incubated for an additional 24 hours. The fluorescence intensity (Excitation at 530 nm, Emission at 580 nm) is quantified using the Acques™ system (Molecular Devices).

Inhibition of Cellular BCR-Abl Dependent Proliferation 32D-p210 cells are plated into 96 well TC plates at a density of 15,000 cells per well. 50 μL of two fold serial dilutions of the test compound (C$_{max}$ is 40 μM) are added to each well (STI571 is included as a positive control). After incubating the cells for 48 hours at 37° C., 5% CO$_2$, 15 μL of MTT (Promega) is added to each well and the cells are incubated for an additional 5 hours. The optical density at 570 nm is quantified spectrophotometrically and IC$_{50}$ values, the concentration of compound required for 50% inhibition, determined from a dose response curve.

Effect on Cell Cycle Distribution 32D and 32D-p210 cells are plated into 6 well TC plates at 2.5×10$^6$ cells per well in 5 ml of medium and test compound at 1 or 10 μM is added (STI571 is included as a control). The cells are then incubated for 24 or 48 hours at 37° C., 5% CO$_2$. 2 ml of cell suspension is washed with PBS, fixed in 70% EtOH for 1 hour and treated with PBS/EDTA/RNase A for 30 minutes. Propidium iodide (Cf=10 μg/ml) is added and the fluorescence intensity is quantified by flow cytometry on the FACScalibur™ system (BD Biosciences). Test compounds of the present invention demonstrate an apoptotic effect on the 32D-p210 cells but do not induce apoptosis in the 32D parental cells.

Effect on Cellular BCR-Abl Autophosphorylation

BCR-Abl autophosphorylation is quantified with capture Elisa using a c-abl specific capture antibody and an antiphosphotyrosine antibody. 32D-p210 cells are plated in 96 well TC plates at $2 \times 10^5$ cells per well in 50 μL of medium. 50 μL of two fold serial dilutions of test compounds ($C_{max}$ is 10 μM) are added to each well (STI571 is included as a positive control). The cells are incubated for 90 minutes at 37° C., 5% $CO_2$. The cells are then treated for 1 hour on ice with 150 μL of lysis buffer (50 mM Tris-HCl, pH 7.4, 150 mM NaCl, 5 mM EDTA, 1 mM EGTA and 1% NP-40) containing protease and phosphatase inhibitors. 50 μL of cell lysate is added to 96 well optiplates previously coated with anti-abl specific antibody and blocked. The plates are incubated for 4 hours at 4° C. After washing with TBS-Tween 20 buffer, 50 μL of alkaline-phosphatase conjugated anti-phosphotyrosine antibody is added and the plate is further incubated overnight at 4° C. After washing with TBS-Tween 20 buffer, 90 μL of a luminescent substrate are added and the luminescence is quantified using the Acquest™ system (Molecular Devices). Test compounds of the invention that inhibit the proliferation of the BCR-Abl expressing cells, inhibit the cellular BCR-Abl autophosphorylation in a dose-dependent manner.

Effect on Proliferation of Cells Expressing Mutant Forms of Bcr-abl

Compounds of the invention are tested for their antiproliferative effect on Ba/F3 cells expressing either wild type or the mutant forms of BCR-Abl (G250E, E255V, T315I, F317L, M351T) that confers resistance or diminished sensitivity to STI571. The antiproliferative effect of these compounds on the mutant-BCR-Abl expressing cells and on the non transformed cells were tested at 10, 3.3, 1.1 and 0.37 μM as described above (in media lacking IL3). The $IC_{50}$ values of the compounds lacking toxicity on the untransformed cells were determined from the dose response curves obtained as describe above.

b-Raf

Compounds of the invention are tested for their ability to inhibit the activity of b-Raf. The assay is carried out in 384-well MaxiSorp plates (NUNC) with black walls and clear bottom. The substrate, IκBα is diluted in DPBS (1:750) and 15 μl is added to each well. The plates are incubated at 4° C. overnight and washed 3 times with TBST (25 mM Tris, pH 8.0, 150 mM NaCl and 0.05% Tween-20) using the EMBLA plate washer. Plates are blocked by Superblock (15 μl/well) for 3 hours at room temperature, washed 3 times with TBST and pat-dried. Assay buffer containing 20 μM ATP (10 μl) is added to each well followed by 100 nl or 500 nl of compound. B-Raf is diluted in the assay buffer (1 μl into 25 μl) and 10 μl of diluted b-Raf is added to each well (0.4 kg/well). The plates are incubated at room temperature for 2.5 hours. The kinase reaction is stopped by washing the plates 6 times with TBST. Phosph-IκBα (Ser32/36) antibody is diluted in Superblock (1:10,000) and 15 μl is added to each well. The plates are incubated at 4° C. overnight and washed 6 times with TBST. AP-conjugated goat-anti-mouse IgG is diluted in Superblock (1:1,500) and 15 μl is added to each well. Plates are incubated at room temperature for 1 hour and washed 6 times with TBST. 15 μl of Attophos AP substrate is added to each well and plates are incubated at room temperature for 15 minutes. Plates are read on Acquest or Analyst GT using a Fluorescence Intensity Nanxin BBT anion (505 dichroic mirror).

Upstate KinaseProfiler™—Radio-Enzymatic Filter Binding Assay

Compounds of the invention are assessed for their ability to inhibit individual members of a panel of kinases (a partial, non-limiting list of kinases includes: Abl, BCR-Abl, EGF-R, c-erbB2 kinase (HER-2), CHK2, FGFR3, p70S6K, PKC, PDGF-R, p38, TGFβ, KDR, c-Kit, b-RAF, c-RAF, FLT1 and FLT4). The compounds are tested in duplicates at a final concentration of 10 μM following this generic protocol. Note that the kinase buffer composition and the substrates vary for the different kinases included in the "Upstate KinaseProfiler™" panel. The compounds are tested in duplicates at a final concentration of 10 μM following this generic protocol. Note that the kinase buffer composition and the substrates vary for the different kinases included in the "Upstate KinaseProfiler™" panel. Kinase buffer (2.5 μL, 10×—containing $MnCl_2$ when required), active kinase (0.001–0.01 Units; 2.5 μL), specific or Poly(Glu4-Tyr) peptide (5–500 μM or 0.01 mg/ml) in kinase buffer and kinase buffer (50 μM; 5 μL) are mixed in an eppendorf on ice. A Mg/ATP mix (10 μL; 67.5 (or 33.75) mM $MgCl_2$, 450 (or 225) μM ATP and 1 μCi/μl [γ-$^{32}$P]-ATP (3000 Ci/mmol)) is added and the reaction is incubated at about 30° C. for about 10 minutes. The reaction mixture is spotted (20 μL) onto a 2 cm×2 cm P81 (phosphocellulose, for positively charged peptide substrates) or Whatman No. 1 (for Poly (Glu4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction.

Compounds of Formula I, in free form or in pharmaceutically acceptable salt form, exhibit valuable pharmacological properties, for example, as indicated by the in vitro tests described in this application. For example, compounds of Formula I preferably show an $IC_{50}$ in the range of $1 \times 10^{-10}$ to $1 \times 10^{-5}$ M, preferably less than 1 μM for wild type BCR-Abl and b-Raf. For example, N-(3-{2-[6-(3-dimethylamino-phenylamino)-pyrimidin-4-yl]-phenylamino}-phenyl)-4-(4-methyl-piperazin-1-ylmethyl)-benzamide (example 1), has an $IC_{50}$ of 0.667 μM for b-Raf.

Compounds of Formula I, at a concentration of 10 μM, preferably show a percentage inhibition of greater than 50%, preferably greater than about 70%, against Abl, BCR-Abl, EGF-R, c-erbB2 kinase (HER-2), CHK2, FGFR3, p70S6K, PKC, PDGF-R, p38, TGFβ, KDR, c-Kit, b-RAF, c-RAF, FLT1 and/or FLT4 kinases. For example, N-(3-{2-[6-(3-dimethylamino-phenylamino)-pyrimidin-4-yl]-phenylamino}-phenyl)-4-(4-methyl-piperazin-1-ylmethyl)-benzamide (example 1), at a concentration of 10 μM, inhibits the following kinases by the percentage shown in brackets (for example, 100% means complete inhibition, 0% means no inhibition): Abl (90%), c-RAF (96%), CHK2 (59%), FGFR3 (56%), p70S6K (79%), PDGFRα (71%) and PKCα (64%).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of formula I:

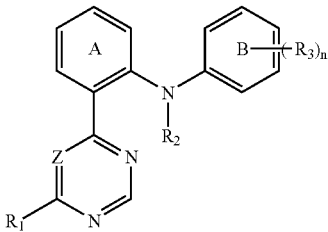

in which:
n is 0, 1, 2 or 3;
Z is =CH—;
$R_1$ is selected from hydrogen and —$NR_4R_5$; wherein $R_4$ is selected from hydrogen and $C_{1-6}$alkyl; and $R_5$ is selected from $C_{6-10}$aryl, $C_{5-10}$heteroaryl, $C_{3-12}$cycloalkyl and $C_{3-8}$heterocycloalkyl, wherein any aryl, heteroaryl, cycloalkyl or heterocycloalkyl of $R_5$ can he optionally substituted by 1 to 3 radicals independently selected from cyano, nitro, halo, $C_{1-6}$alkyl, halo-substituted-$C_{1-6}$alkyl, $C_{1-6}$alkoxy, halo-substituted-$C_{1-6}$alkoxy and —$NR_6R_7$; wherein $R_6$ and $R_7$ are independently selected from hydrogen and $R_{1-6}$alkyl;
$R_2$ is selected from hydrogen and $C_{1-6}$alkyl;
$R_3$ is selected from halo, cyano, nitro, $C_{1-6}$alkyl, halo-substituted-$C_{1-6}$alkyl, $C_{1-6}$alkoxy, halo-substituted-$C_{1-6}$ alkoxy, —$XNR_8R_8$, —$XNR_8R_9$, —$XC(O)R_8$, —$XNR_8C(O)R_9$ and —$XC(O)NR_8R_9$; wherein X is a bond or $C_{1-4}$alkylene, $R_8$ is selected from hydrogen and $C_{1-6}$alkyl, and $R_9$ is selected from $C_{6-10}$aryl, $C_{5-10}$heteroaryl, $C_{3-12}$cycloalkyl and $C_{3-6}$heterocycloalkyl; wherein any aryl, heteroaryl, cycloalkyl or heterocycloalkyl of $R_9$ is optionally substituted by a radical selected from halo-substituted-$C_{1-6}$alkyl, —$XOR_8$, —$XR_{10}$, —$XS(O)_2N(OR_8)_2$, —$XS(O)N(XOR_8)_2$, —$XSN(OR_8)_2$, —$XSR_{10}$, —$XS(O)R_{10}$ and —$XS(O)_2R_{10}$; wherein X is a bond or $C_{1-6}$alkylene, $R_8$ is hydrogen or $C_{1-6}$alkyl, and $R_{10}$ is a radical selected from $C_{3-8}$heterocycloalkyl and $C_{5-10}$heteroaryl; wherein any heterocycloalkyl or heteroaryl of $R_{10}$ is optionally substituted by 1 to 3 radicals independently selected from halo, cyano, nitro, $C_{1-6}$alkyl, halo-substituted-$C_{1-6}$alkyl, $C_{1-6}$alkoxy, halo-substituted-$C_{1-6}$alkoxy; and any one ring carbon of $R_{10}$ is optionally replaced by —C(O)—; and wherein the phenyl rings A and B can have up to four —C= groups replaced by —N=; or a pharmaceutically acceptable salt thereof.

2. The compound of claim 1 in which:
$R_1$ is selected from hydrogen and —$NR_4R_5$; wherein $R_4$ is selected from hydrogen and $C_{1-6}$alkyl; and $R_5$ is $C_{6-10}$alkyl optionally substituted by 1 to 3 radicals independently selected from halo-substituted-$C_{1-6}$alkyl and —$NR_6R_7$; wherein $R_6$ and $R_7$ are independently selected from hydrogen and $C_{1-6}$alkyl; and
$R_2$ is selected from hydrogen and $C_{1-6}$alkyl;
$R_3$ is selected from halo, $C_{1-6}$alkyl, —$XC(O)R_8$, —$XNR_8R_8$, —$XNR_8C(O)R_9$ and —$XC(O)NR_8R_9$; wherein X is a bond or $C_{1-4}$alkylene, $R_8$ is selected from hydrogen and $C_{1-6}$alkyl, and $R_9$ is selected from $C_{6-10}$aryl and $C_{3-12}$cycloalkyl; wherein any aryl or cycloalkyl of $R_9$ is optionally substituted by a radical selected from —$XOR_8$, —$XR_{10}$, —$XS(O)_2N(XOR_8)_2$ and —$XS(O)_2R_{10}$; wherein X is a bond or $C_{1-6}$alkylene, $R_8$ is hydrogen or $C_{1-6}$alkyl, and $R_{10}$ is a radical selected from $C_{3-8}$heterocycloalkyl and $C_{5-10}$heteroaryl; wherein any heterocycloalkyl or heteroaryl of $R_{10}$ is optionally substituted by 1 to 3 $C_{1-6}$alkyl groups; and any one ring carbon of $R_{10}$ is optionally replaced by —C(O)—.

3. The compound of claim 2 in which:
$R_1$ is selected from hydrogen and —$NHR_5$; wherein $R_5$ is phenyl optionally substituted by 1 to 3 radicals independently selected from trifluoromethyl and dimethylamino; and $R_2$ is hydrogen.

4. The compound of claim 2 in which:
$R_3$ is selected from halo, methyl, formyl, dimethylamino, —NHC(O)$R_9$ and —C(O)NH$R_9$; wherein $R_9$ is selected from phenyl and cyclopropyl; wherein any aryl or cycloalkyl of $R_9$ is optionally substituted by a radical selected from —$CH_2OH$, —$XR_{10}$, —$S(O)_2N(C_2H_4OH)_2$ and —$S(O)_2R_{10}$; wherein X is a bond or methylene, and $R_{10}$ is a radical selected from piperazinyl, morpholino and 5-oxo-4,5-dihydro-pyrazol-1-yl; wherein any heterocycloalkyl or heteroaryl of $R_{10}$ is optionally substituted by 1 to 3 methyl groups.

5. The compound of claim 2 in which $R_4$ is selected from halo, trifluoromethyl and —$XR_{10}$; wherein X is a bond or methylene; $R_{10}$ is selected from imidazolyl, piperazinyl and morpholino; wherein any heteroaryl or heterocycloalkyl is optionally substituted with methyl.

6. The compound of claim 1 selected from: N-(3-{2-[6-(3-Dimethylamino-phenylamino)-pyrimidin-4-yl]-phenylamino}-phenyl)-4-(4-methyl-piperazin-1-ylmethyl)-benzamide; N-(3-{2-[6-(4-Trifluoromethyl-phenylamino)-pyrimidin-4-yl]-phenylamino}-phenyl)-benzamide; 4-(4-Methyl-piperazin-1-ylmethyl)-N-(3-{2-[6-(4-trifluoromethyl-phenylamino)-pyrimidin-4-yl]-phenylamino}-phenyl)-benzamide; N-(3-{2-[6-(3-Dimethylamino-phenylamino)-pyrimidin-4-yl]-phenylamino}-phenyl)-4-hydroxymethyl-benzamide; N-(3-{2-[6-(3-Dimethylamino-phenylamino)-pyrimidin-4-yl]-phenylamino}-phenyl)-3-(morpholine-4-sulfonyl)-benzamide; N-(3-{2-[6-(3-Dimethylamino-phenylamino)-pyrimidin-4-yl]-phenylamino}-phenyl)-4-(3-methyl-5-oxo-4,5-dihydro-pyrazol-1-yl)-benzamide; N-(3-{2-[6-(3-Dimethylamino-phenylamino)-pyrimidin-4-yl]-phenylamino}-phenyl)-3-(4-methyl-piperazine-1-sulfonyl)-benzamide; 4-[Bis-(2-hydroxy-ethyl)-sulfamoyl]-N-(3-{2-[6-(3-dimethylamino-phenylamino)-pyrimidin-4-yl]-phenylamino}-phenyl)-benzamide; 4-(4-Methyl-piperazin-1-ylmethyl)-N-[3-(2-pyrimidin-4-yl-phenylamino)-phenyl]-benzamide; N-Cyclopropyl-3-{2-[6-(4-trifluoromethyl-phenylamino)-pyrimidin-4-yl]-phenylamino}-benzamide; {6-[2-(3-Fluoro-phenylamino)-phenyl]-pyrimidin-4-yl}-(4-trifluoromethyl-phenyl)-amine; {6-[2-(2-Fluoro-phenylamino)-phenyl]-pyrimidin-4-yl}-(4-trifluoromethyl-phenyl)-amine; {6-[2-(4-Fluoro-phenylamino)-phenyl]-pyrimidin-4-yl}-(4-trifluoromethyl-phenyl)-amine; {6-[2-(2-Chloro-phenylamino)-phenyl]-pyrimidin-4-yl}-(4-trifluoromethyl-phenyl)-amine; {6-[2-(3-Chloro-phenylamino)-phenyl]-pyrimidin-4-yl}-(4-trifluoromethyl-phenyl)-amine; {6- [2-(4-Chloro-phenylamino)-phenyl]-pyrimidin-4-yl}-(4-trifluoromethyl-phenyl)-amine; [6-(2-o-Tolylamino-phenyl) -pyrimidin-4-yl]-(4-trifluoromethyl-phenyl)-amine; [6-(2-m-Tolylamino-phenyl)-pyrimidin-4-yl]-(4-trifluoromethyl-phenyl)-amine; [6-(2-p-Tolylamino-phenyl)-pyrimidin-4-yl]-(4-trifluoromethyl-phenyl)-amine; 3-{2-[6-(4-Trifluoromethyl-phenylamino)-pyrimidin-4-yl]-phenylamino}-benzaldehyde; 4-{2-[6-(4-Thfluoromethylphenylamino)-pyrimidin-4-yl]-phenylamino}-benzaldehyde; (4-Trifluoromethyl-phenyl)-{6-[2-(2-trifluoromethyl-phenylamino)-phenyl]-pyrimidin-4-yl}-amine; (4-Trifluoromethyl-phenyl) -{6-[2-(4-trifluoromethyl-phenylamino)-phenyl]-pyrimidin-4-yl}-amine; N,N -Dimethyl-N'-{2-[6-(4-tritluoromethyl-phenylamino)-pyrimidin-4-yl]-phenyl}-benzene-1,4-diamine; Phenyl-[6-(2-phenylamino-phenyl)-pyrimidin-4-yl]-amine; {6-[2-(2,6-Dichloro-phenylamino) -phenyl]-pyrimidin-4-yl}-(3,4,5-trimethoxy-phenyl)-amine; and {6-[2-(2,6-Dichloro-phenylamino)-phenyl]-pyrimidin-4-yl}-[4-(4-methyl-piperazin-1-yl)-phenyl]-amine.

7. A pharmaceutical composition comprising a therapeutically effective amount of a compound of claim 1 in combination with a pharmaceutically acceptable excipient.

* * * * *